US006611965B1

(12) United States Patent
Lee

(10) Patent No.: US 6,611,965 B1
(45) Date of Patent: Sep. 2, 2003

(54) SAFETY GOGGLES

(76) Inventor: Shu-Min Lee, No. 57, Kao-Kuang-Liu St., Yungkang City, Tainan Hsien (TW)

( * ) Notice: Subject to any disclaimer, the term of this patent is extended or adjusted under 35 U.S.C. 154(b) by 0 days.

(21) Appl. No.: 10/328,151

(22) Filed: Dec. 23, 2002

(51) Int. Cl.[7] .................................................. A61F 9/02
(52) U.S. Cl. ............................................ 2/431; 2/450
(58) Field of Search ............................ 2/431, 450, 452

(56) References Cited

U.S. PATENT DOCUMENTS

| | | | | |
|---|---|---|---|---|
| 5,915,541 A | * | 6/1999 | Beltrani ........................ | 2/430 |
| 6,047,410 A | * | 4/2000 | Dondero ....................... | 2/426 |
| 6,079,054 A | * | 6/2000 | Chou ............................ | 2/428 |
| 6,105,177 A | * | 8/2000 | Paulson et al. ................ | 2/431 |

* cited by examiner

Primary Examiner—John J. Calvert
Assistant Examiner—Katherine Moran
(74) Attorney, Agent, or Firm—William E. Pelton, Esq.

(57) ABSTRACT

Safety goggles for sports and work includes a frame, two lenses, two female fasteners and an elastic band. The frame has two opposite edges and a connector is formed integrally from each edge of the frame. Two socket holes are defined through the frame. A lock hole is defined in each lens, and a lens is mounted in each socket hole in the frame. Each female fastener has a lock hook that is formed integrally on an attachment element. The elastic band is coupled to the connector by means of the female fastener, and the lock hook is hooked in the lock hole in the lens to prevent the lens from popping out of the socket hole in the frame.

4 Claims, 2 Drawing Sheets

SAFETY GOGGLES

BACKGROUND OF THE INVENTION

1. Field of the Invention

The present invention relates to safety goggles, and more particularly to safety goggles suitably used for sports and work.

2. Description of Related Art

People who work in hazardous environments or operate dangerous machinery need to wear goggles to protect their eyes. Also, many sport players wear goggles to keep wind, sweat, dust or the like from interfering with their vision. Conventional goggles generally include a frame, two lenses and an elastic band. Two socket holes are defined in the frame through which the eyes of a user see. The lenses are mounted in the socket holes in the frame respectively by wedging, bonding or the like. The elastic band has two ends and wraps around the head of the user. Each end of the band is connected to an edge of the frame.

When the user wears the goggles, the elastic band is stretched and wound around the head of the user. A restitution force is created in the elastic band, and the restitution force of the elastic band is applied to tighten the goggles on the head. Unfortunately, the restitution force of the elastic band may deform the frame because the ends of the elastic band are coupled to the edges of the frame. Furthermore, the user will pull the elastic band to adjust the goggles on the head any time, and the frame will be deformed again and again. After extensive use, deformation of the frame will cause the lenses to pop out of the socket holes of the frame or crack a lens.

To overcome the shortcomings, the present invention tends to provide a pair of safety goggles to mitigate or obviate the aforementioned problems.

SUMMARY OF THE INVENTION

The main objective of the invention is to provide a pair of safety goggles that will prevent a lens from popping out of a socket hole of a frame of the safety goggles.

Other objectives, advantages and novel features of the invention will become more apparent from the following detailed description when taken in conjunction with the accompanying drawings.

DETAILED DESCRIPTION OF PREFERRED EMBODIMENT

Figure 1:
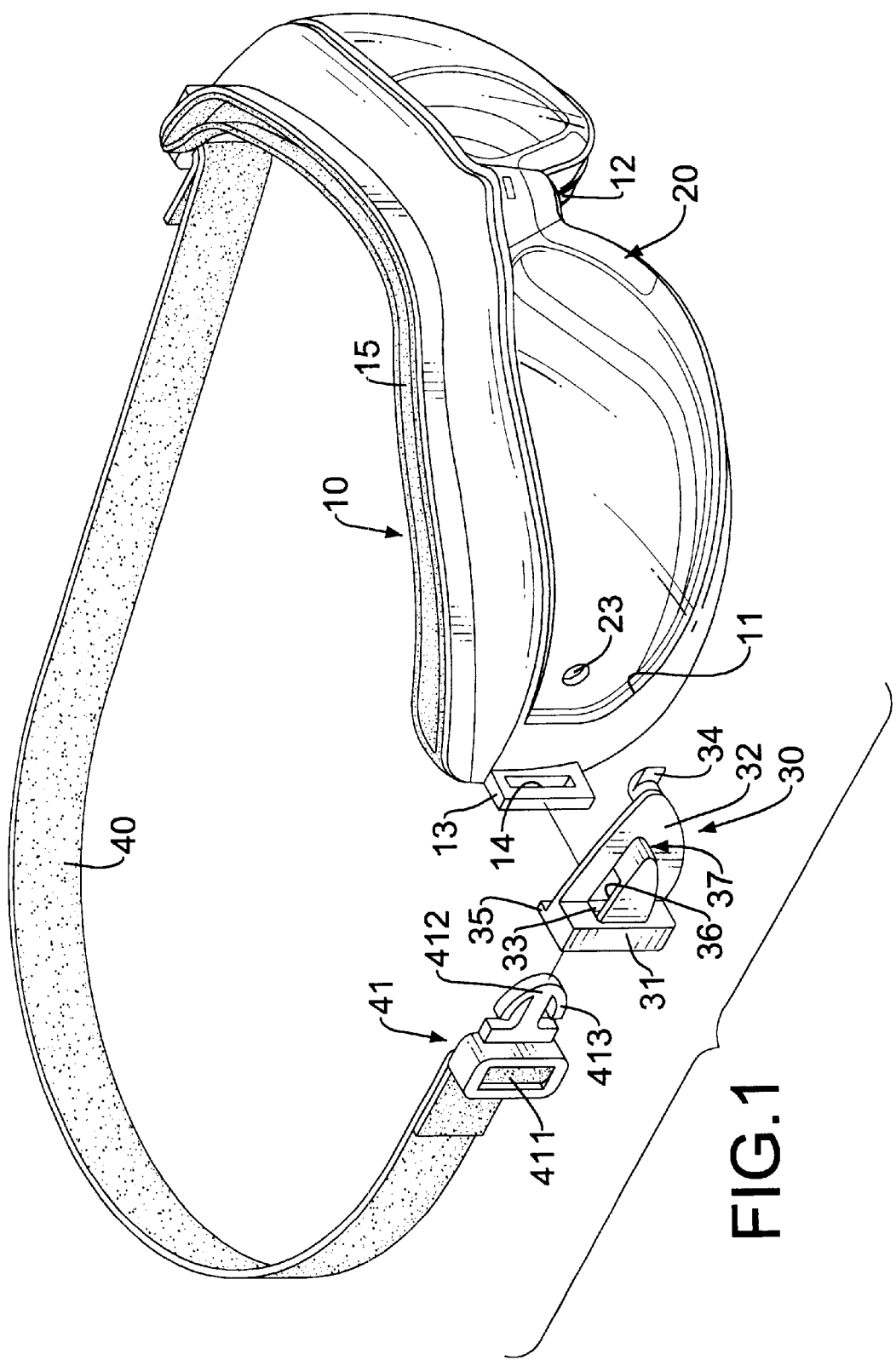
FIG. 1 is a perspective view of safety goggles in accordance with the present invention.
Figure 2:
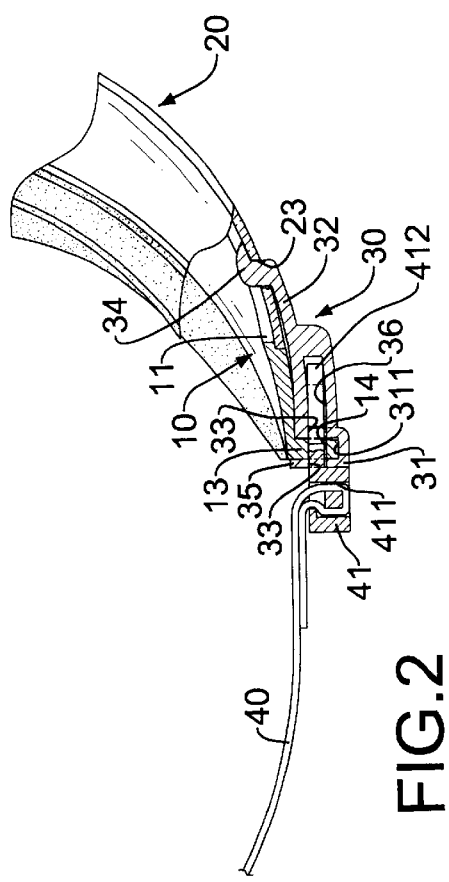
FIG. 2 is an enlarged top plan view in partial section of the safety goggles in FIG. 1.
Figure 3:
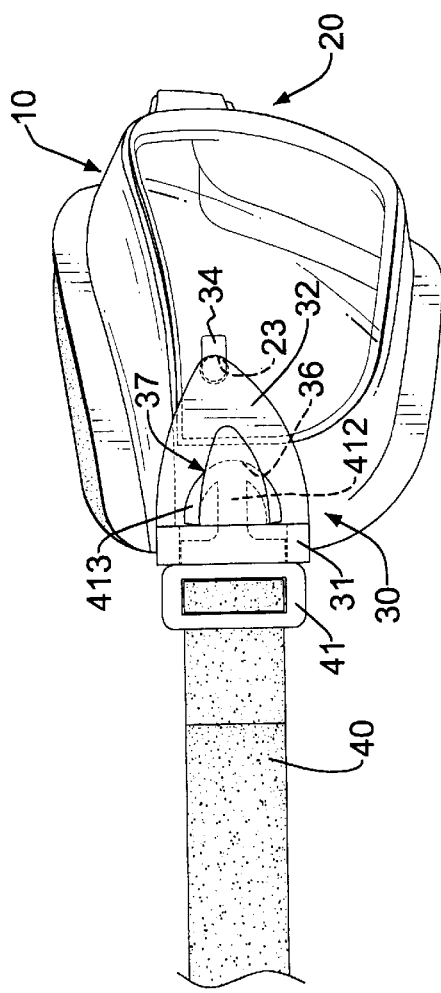
FIG. 3 is a partial side plan view of the safety goggles in FIG. 1.

With reference to FIGS. 1 to 3, safety goggles in accordance with the present invention includes a frame assembly, two lenses (20), two female fasteners (30) and a band assembly. The frame assembly includes a frame (10), a nose pad (12) and a forehead seal (15). The frame (10) has a top (not numbered), a bottom (not numbered), a face attachment side (not numbered), two opposite edges (not numbered) and two socket holes (11). The nose pad (12), is soft, is attached centrally to the bottom of the frame (10) and is adapted to abut a human's nose. The forehead seal (15) is made of elastic material such as rubber or plastic and is attached securely to the face attachment side at the top of the frame (10). Also, the forehead seal (15) is used to absorb vibration or shock during sporting or working activities and let users feel comfortable when wearing the safety goggles. Several small vapor exhaust holes (not shown) are defined in the forehead seal (15), which provide means for humid vapors to escape. A connector (13) with a fitting hole (14) defined in the connector (13) is formed integrally at each edge of the frame (10) and is adapted to connect to the female fastener (30).

The lenses (20) are transparent, are mounted in the respective socket holes (11) in the frame (10) and protect the eyes of the user. A lock hole (23) is defined in each lens (20) near the connector (13).

The female fastener (30) has a connecting end (31), an attachment element (32), a lock hook (34) and a cover (37). The attachment element (32) has an inside surface (not numbered), an outside surface (not numbered), a front edge (not numbered) and a rear edge (not numbered). The inside surface of the attachment element (32) abuts the frame (10). A transverse fitting recess (311) is formed in the connecting end (31) through the inside surface at the rear edge of the attachment element (32), faces the connector (13) of the frame (10) and is adapted to hold the connector (13) in place. The lock hook (34) is formed integrally on the inside surface at the front edge of the attachment element (32), and the cover (37) is formed integrally from the connecting end (31) toward the lock hook (34) on the outside surface of the attachment element (31).

A lip (35) is formed integrally with and extends from the inside rear edge of the attachment element (32) A fastener hole (33) is defined through the connecting end (31) and communicates with the fitting recess (311). An arm hole (36) with a top opening (not numbered) and a bottom opening (not numbered) is defined vertically through the cover (37) and communicates with both the fastener hole (33) and the fitting recess (311) in the connecting end (31).

The band assembly includes a band (40) and two male fasteners (41). The band (40) has two ends, and each of the ends of the band (40) is attached to opposite edges of the frame (10), respectively. The male fastener (41) has a buckle (411) and an anchor-shaped hook (412) with two elastic arms (413). Each end of the band (40) is threaded through one of the buckles (411), respectively. The anchor-shaped hook (412) is formed integrally with the buckle (411) and is adapted to be mounted in the fastener hole (33) in the connecting end (31) of the female fastener (30). The elastic arms (413) of the anchor-shaped hook (412) respectively extend out of the top and bottom openings of the arm hole (36) in the cover (37).

To use the safety goggles, the length of the band (40) can be adjusted to fit around the user's head. The lock hook (34) is mounted in the lock hole (23) in the lens (20) and the connecting end (31) is pressed toward the frame (10). The connector (13) is held in the recess (311) so the lip (35) abuts the edge of the frame (10). The fitting hole (14) and the fastener hole (33) are aligned, and the elastic arms (413) pass through the fastener hole (33) and are received in the arm hole (36). The elastic arms (413) of the anchor-shaped hook (412) extend out of the arm hole (36) to hold the male fastener (41) in the female fastener (30) and the connector (13).

To release the band (40) from the frame (10), the elastic arms (413) of the anchor-shaped hook (412) are pressed together until the anchor-shaped hook (412) slides through the fastener hole (33). Thus, the male fastener (41) will disengage from the female fastener (30) so the safety goggles can be removed.

Consequently, no matter how many times the safety goggles are pulled down and the band (40) are connected or released, the socket hole (11) in the frame (10) is not deformed excessively. The method of putting on and removing the safety goggles can also prevent the lens (20) from popping out of the socket holes (11) in the frame (10).

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

At is claimed is:

1. A pair of safety goggles comprising:
   a frame assembly comprising
      a frame with a top, a bottom, two opposite edges, a face attachment side and two socket holes defined through the frame;
      a nose pad attached centrally at the bottom and between the two socket holes in the frame and adapted to rest on a user's nose;
      an elastic forehead seal attached to the top of the face attachment side of the frame; and
      a connector with a fitting hole defined laterally therein formed integrally from each respective one of the opposite edges of the frame;
   two lenses respectively mounted in the socket holes in the frame to protect eyes of the user, and a lock hole defined in each lens near the edge of the frame;
   two female fasteners for connecting respectively to the connectors on the frame, and each female fastener having
      an attachment element having an inside surface, an outside surface, a front edge and a rear edge, and the inside surface of the attachment element attached to the frame;
      a connecting end with a fitting recess for receiving the connector of the frame defined therein formed integrally from the outside surface and at the rear edge of the attachment element, and the fitting recess defined through the inside surface of the attachment element;
      a lock hook corresponding to the lock hole in the corresponding one of the lenses and formed integrally from the inside surface at the front edge of the attachment element;
      a cover formed integrally from the connecting end toward the lock hook on the outside surface of the attachment element;
      a fastener hole defined through the connecting end and communicating with the fitting recess; and
      an arm hole with a top opening and a bottom opening defined through the cover and communicating with both the fastener hole and the fitting recess; and
   a band assembly comprising
      an elastic band with two ends and adapted for fitting with a head of the user;
      two male fasteners respectively attached to the ends of the elastic band and attached to the female fasteners;
   wherein the fitting hole in each connector and the fastener hole in the corresponding one of the female fasteners are aligned to hold the corresponding one of the male fasteners, and the lock hook on each respective female fastener is hooked in the lock hole in the corresponding one of the lens.

2. The safety goggles as claimed in claim 1 further comprising
   a lip formed integrally from the inside surface at the rear edge of the attachment element.

3. The safety goggles as claimed in claim 2, wherein the male fastener has
   two buckles respectively attached to opposite ends of the elastic band;
   an anchor-shaped hook with two elastic arms formed integrally from each buckle and adapted to insert into the fastener hole in the corresponding one of the female fasteners and the fitting hole in the corresponding connector and the two elastic arms respectively extending out of the top and the bottom openings of the extending hole in the corresponding female fastener.

4. The safety goggles as claimed in claim 1, wherein the male fastener has
   two buckles are respectively attached to opposite ends of the elastic band;
   an anchor-shaped hook with two elastic arms formed integrally from the buckle and adapted to insert into the fastener hole in the corresponding one of the female fasteners and the fitting hole in the corresponding connector and the two elastic arms respectively extending out of the top and the bottom openings of the extending hole in the corresponding female fastener.

* * * * *